(12) United States Patent
Frantz

(10) Patent No.: US 11,308,290 B2
(45) Date of Patent: Apr. 19, 2022

(54) MIXED SIGNAL COMPUTER ARCHITECTURE

(71) Applicant: Octavo Systems LLC, Sugar Land, TX (US)

(72) Inventor: Gene Alan Frantz, Sugar Land, TX (US)

(73) Assignee: OCTAVO SYSTEMS LLC, Sugar Land, TX (US)

( * ) Notice: Subject to any disclaimer, the term of this patent is extended or adjusted under 35 U.S.C. 154(b) by 3 days.

(21) Appl. No.: 16/605,718

(22) PCT Filed: Apr. 16, 2018

(86) PCT No.: PCT/US2018/027721
§ 371 (c)(1),
(2) Date: Oct. 16, 2019

(87) PCT Pub. No.: WO2018/194952
PCT Pub. Date: Oct. 25, 2018

(65) Prior Publication Data
US 2020/0134268 A1 Apr. 30, 2020

Related U.S. Application Data

(60) Provisional application No. 62/486,350, filed on Apr. 17, 2017.

(51) Int. Cl.
*G06J 1/00* (2006.01)
*G06F 7/483* (2006.01)
*G06F 7/57* (2006.01)
*G06G 7/06* (2006.01)
*H03M 1/02* (2006.01)
*H03M 1/18* (2006.01)

(52) U.S. Cl.
CPC ............... *G06J 1/00* (2013.01); *G06F 7/483* (2013.01); *G06F 7/57* (2013.01); *G06G 7/06* (2013.01); *H03M 1/02* (2013.01); *H03M 1/18* (2013.01)

(58) Field of Classification Search
CPC ........................................................ G06J 1/00
See application file for complete search history.

(56) References Cited

U.S. PATENT DOCUMENTS

| 3,185,821 A * | 5/1965 | Lee ........................... G09B 9/20 708/800 |
| 4,613,974 A | 9/1986 | Vokac et al. |
| 4,951,054 A | 8/1990 | Kohdaka |
| 5,107,146 A | 4/1992 | El-Ayat |

(Continued)

OTHER PUBLICATIONS

International Search Report and Written Opinion issued for International Application No. PCT/US2018/027721 dated Sep. 6, 2018, 17 pages.

*Primary Examiner* — Chuong D Ngo
(74) *Attorney, Agent, or Firm* — Rothwell, Figg, Ernst & Manbeck, P.C.

(57) ABSTRACT

The present disclosure describes a computer using a combination of analogue and digital components/elements used in a cohesive manner. Depending on the signals and data the computer manipulates, the analog processing elements and digital processing elements can be used separately, independently or in combination to optimize the computational results and the performance of the computer.

17 Claims, 22 Drawing Sheets

(56) References Cited

U.S. PATENT DOCUMENTS

| | | | |
|---|---|---|---|
| 5,566,103 A | 10/1996 | Hyatt | |
| 6,208,542 B1 | 3/2001 | Wang et al. | |
| 6,724,220 B1 | 4/2004 | Snyder et al. | |
| 7,233,551 B2 * | 6/2007 | Abe | G11B 7/005 |
| | | | 369/47.2 |
| 8,270,266 B2 * | 9/2012 | Lin | G11B 20/10046 |
| | | | 369/44.27 |
| 9,143,134 B1 | 9/2015 | Kutz et al. | |
| 2006/0036667 A1 | 2/2006 | Srivastava | |
| 2008/0209170 A1 | 8/2008 | Mueller et al. | |

\* cited by examiner

FIG. 12A

| Instruction | Action | Digital | Analog | Mixed Signal | Execution |
|---|---|---|---|---|---|
| Multiply | a * b = c | MPY | MPYA | | multiply the value in register a by the value in register b and put the result in register c |
| Multiply | a * b = c | | | MPYAD | multiply the value in analog register a by the value in analog register b and put the result in digital register c |
| Multiply | a * b = c | | | MPYDA | multiply the value in digital register a by the value in digital register b and put the result in analog register c |
| Addition | a + b = c | ADD | ADDA | | add the value in register a to the value in register b and put the result in register c |
| Addition | a + b = c | | | ADDAD | add the value in analog register a to the value in analog register b and put the result in digital register c |
| Addition | a + b = c | | | ADDDA | add the value in digital register a to the value in digital register b and put the result in analog register c |
| Subtraction | a - b = c | SUB | SUBA | | subtract the value in register b from the value in register a and put the result in register c |
| Subtraction | a - b = c | | | SUBAD | subtract the value in analog register b from the value in analog register a and put the result in digital register c |
| Subtraction | a - b = c | | | SUBDA | subtract the value in digital register b from the value in digital register a and put the result in analog register c |
| Divide | a/b = c | DIV | DIVA | | divide the value in register a by the value in register b and put the result in register c |
| Divide | a/b = c | | | DIVAD | divide the value in analog register a by the value in analog register b and put the result in digital register c |
| Divide | a/b = c | | | DIVDA | divide the value in digital register a by the value in digital register b and put the result in analog register c |

| Instruction | Action | OpCode | Execution |
|---|---|---|---|
| Multiply | Multiply two mixed signal floating point numbers together | MPYMF | Perform an analog multiply in the analog ALU using the data stored in the specified analog registers, perform an addition in the digital ALU using the data stored in the specified digital registers, store the results in the specified analog and digital registers. |
| Multiply | Multiply a mixed signal floating point number by a fixed point number | MPYMFA | Perform an analog multiply in the analog ALU using the data stored in the specified analog registers, store the results in the specified analog registers. |
| Add | Add two mixed signal floating point numbers together | ADDMF | Normalize the exponent and mantissa of the values to be added using the AGC and shifter, place them back into the specified register locations, perform an analog addition in the analog ALU using the data stored in the specified analog registers, perform an addition in the digital ALU using the data stored in the specified digital registers, store the results in the specified analog and digital registers. |
| Subtract | Subtract one mixed signal floating point number from another one | SUBMF | Normalize the exponent and mantissa of the values to be subtracted using the AGC and shifter, place them back into the specified register locations, perform an analog subtraction in the analog ALU using the data stored in the specified analog registers, use the AGC and shifter to normalize the resultant mantissa, place the resultant mantissa in the specified analog register, place the normalized exponent in the specified digital register registers. |
| Divide | Divide a mixed signal floating point number by another one | DIVMF | Take data in two specified analog registers and divide the first by the second and place the result in a specified register, take data in the two digital registers and add them together and place the result in the specified register. |
| Divide | Divide a mixed signal floating point number by a fixed point number. | DIVMFF | Take data in two specified analog registers and divide the first by the second and place the result in a specified register, take data in the digital register for the mixed signal floating point number and place the result in the specified register. |
| FloatM | Use both analog and digital memory location to store a Mixed Signal Floating point | fltM | Create a floating point memory location where the mantissa is in an analog memory and the exponent is in digital memory |
| Load flt pt | Load data into both the digital and analog ALU registers and instruct both ALUs it is a floating point number. | LoadMF | Load into a specific digital register the exponent and into a specific analog register the mantissa, alert both ALUs that the registers are to be used as a mixed signal floating point representation. |
| Store flt pt | Store data in the analog and digital ALU to a memory location and set a flag to indicate it is a floating point number. | StoreMF | Store from a specified digital and analog register the floating point representation into a specified memory location, set a flag in the memory location indicating the data representation is a floating point number |

| Instruction | Action | Digital | Analog | Mixed Signal | Execution |
|---|---|---|---|---|---|
| Greater Than | a > b | | GRT | | from second specified register and store larger in third register |
| Greater Than | | | | GRTM | Take data in specified analog register, compare it to data from a second specified analog register, store larger in third analog register and digital register |
| Less Than | a < b | | LESS | | Take data in specified register, compare it to data from second specified register and store smaller in third register |
| Less Than | | | | LESSM | Take data in specified register, compare it to data from second specified register and store smaller in third analog register and digital register |

| Instruction | Action | Digital | Analog | Mixed Signal | Execution |
|---|---|---|---|---|---|
| EXCHAD | Aa --> Da | | | EXCHAD | Move data from a specified analog register to a specified digital regester |
| EXCHDA | Da --> Aa | | | EXCHDA | Move data from a specified digital register to a specified analog regester |

MIXED SIGNAL COMPUTER ARCHITECTURE

CROSS REFERENCE TO RELATED APPLICATION

This application is a 35 U.S.C. § 371 National Stage of International Patent Application No. PCT/US2018/027721, filed Apr. 16, 2018, designating the United States, which claims the benefit of U.S. Provisional Application No. 62/486,350, which was filed Apr. 17, 2017, the disclosures of which are incorporated herein in their entirety by reference.

TECHNICAL FIELD

Aspects of the present disclosure relate to computers using both analog and digital elements that work together.

BACKGROUND

Often, today's world of real time computing is digital. But before the digital computer became the dominant method of computing, the analog computer was the primary way to handle real time signal processing, for instance, analog computing elements have been used to take signals from the real world and process them in order to properly control various machines or guided weapons.

In some respects, the digital computer appeared to overcome multiple issues with aspects of analog computing, such as noise, drift, and accuracy. During the decades of the 1960s and 1970s, Digital Signal Processing emerged and allowed digital computers to manipulate the real world analog signals once they were sampled and converted to digital signals. Indeed, Digital Signal Processing performed well in meeting the needs of the industry during the last five decades. Digital processing has been used, for instance, in: cell phones; digital music; digital TV; autonomous vehicles; and medical diagnostic tools. However, digital signal processing computers are not keeping up with the demands of the signals and opportunities that are emerging.

Accordingly, there remains a need for effective mixed signal computing architectures. Some emerging opportunities and their applications will demand a combination of analog and digital computing elements integrated together. There are things that a digital computer does best and there are things that an analog computer does best.

SUMMARY

Aspects of the disclosure provide for a Mixed Signal Computer which allow a system designer to seamlessly move back and forth from analog to digital, and back to analog depending on the data being processed and the algorithms used for processing the data.

Aspects of the present disclosure may take advantage of new opportunities in imaging, Internet of Things ("IoT"), and cloud computing, which have stretched the digital computer to its limits. For instance, some embodiments describe a computer containing a combination of analog and digital components/elements, and using both in a cohesive manner. Depending on the signals and data the computer manipulates, the analog processing elements and digital processing elements can be used separately, independently, or in combination to optimize the computational results and the performance of the computer. Using mixed signal processing according to certain embodiments, one may not need to choose between digital and analog computing.

According to some embodiments, a signal processor is described. The processor may be a mixed signal processor having one more digital arithmetic logic units (ALUs) and one or more analog ALUs. The ALUs are arranged with one or more operative communication paths interconnected between the ALUs. In certain aspects, these operative communication paths may comprise one or more exchange registers interconnected with the digital ALU and the analog ALU, where the exchange registers are at least configured for use in converting digital data to analog data and analog data to digital data. In certain aspects, at least one of the exchange registers is configured to perform at least one of (1) generating a first converted value by converting a first value from the digital ALU to an analog value and providing the first converted value to the analog ALU and (2) generating a second converted value by converting a second value from the analog ALU to a digital value and providing the second converted value to the digital ALU. For example, the digital ALU and the analog ALU can be configured to process a common set of data using the operative communication paths.

According to some embodiments, a mixed signal computer is provided. The mixed signal computer may include, for instance: one or more digital ALUs; one or more digital registers, where at least one of the digital registers is connected to least one of the digital ALUs; one or more analog ALUs; one or more analog registers, where at least one of the analog registers is connected to least one of the analog ALUs; and one or more exchange registers, where the exchange registers are interconnected with at least one of the digital registers and at least one of the analog registers. The computer may also include a control unit, a digital memory, and an analog memory. In certain aspects, the control unit can be configured to control the one or more digital ALUs, the one or more analog ALUs, and the one or more exchange registers.

In certain aspects, the computer may also include a plurality of inputs, where at least one of said inputs is analog and at least one of the inputs is digital, and a plurality of outputs, where at least one of the outputs is analog and at least one of the outputs is digital. In certain aspects, the analog input is mapped to the analog memory and the digital input is mapped to the digital memory. In certain aspects, the analog output is mapped to the analog memory and the digital output is mapped to the digital memory. In certain aspects, the one or more analog ALUs may operate continuously responsive to a set of instructions from the control unit, while other analog ALUs may operate using a clock signal independent of the clock signal operating the one or more digital ALUs. In certain aspects, one or more of a set of analog to digital converters and a set of digital to analog converters is connected between the digital and analog registers.

In some embodiments, the computer may also include an automatic gain control circuit controlled by the control unit to scale data values stored in said analog memory and a data shifter controlled by the control unit to scale data values stored in the digital memory. In some embodiments, a mantissa of a data value is stored in the analog memory and an exponent for said mantissa of a stored value is stored in the digital memory.

In certain aspects, a digital and analog memory are configured to use a common set of control and data lines and at least one of a digital and analog memory is connected to a digital control unit and/or at least one of the ALUs. In some embodiments, the control unit is configured such that analog data words are written into both the analog and the digital memories using the same address. In some embodiments, data written into the analog memory is converted to a digital format and stored at the corresponding address location in a digital format in the digital memory. In some embodiments, a flag is set in a register indicating the conversion.

In certain aspects, a control unit is configured such that digital data words are written into both analog and digital memories using the same address, where data written into the digital memory is converted to an analog format and stored at the corresponding address location in the analog format in the analog memory. In some embodiments, a flag is set in a register indicating the conversion. In some embodiments, one or more of the analog and digital memories, the analog and digital ALUs, and the analog and digital registers are selectively synchronized based on at least one of the following: a sample clock, an instruction from a control unit, or an interrupt.

In certain aspects, a set of registers are employed to identify when one or more of an analog memory location is refreshed based on its digital counterpart, a digital memory location is refreshed based on its analog counterpart, a digital memory location is refreshed based on an equivalent analog memory update, and an analog memory location is directly refreshed. In some embodiments, a digital ALU is provided with intermediate results from an analog ALU, based on at least one of the following: a predetermined instruction from a control unit, a clock set up by the control unit, and a predetermined interrupt set up by the control unit. In some embodiments, the analog ALU is provided with intermediate results from the digital ALU, responsive to a predetermined instruction from the control unit. In some embodiments, the computer further includes memory synchronization means.

According to some embodiments, an exchange register is provided. It may include, for instance: a digital register with two or more bits connected to a digital ALU; an analog register connected to an analog ALU; an analog to digital converter connected to the analog and digital registers; a digital to analog converter connected to the digital and analog registers; an automatic gain control circuit to scale data in the analog register; a data shifter circuit to scale data in the digital register; a controller; and a memory. In certain aspects, the controller is configured to manage the exchange register based on instructions or commands stored in a memory.

According to some embodiments, a method for performing mixed signal computations is described. The method may begin with reading a first value from a digital ALU and generating a first converted value by converting the first value from the digital ALU to an analog value using a digital to analog (D/A) converter. The method may also include storing the first converted value in an analog ALU and processing the first converted value using the analog ALU. The method may also include reading a second value from an analog ALU and generating a second converted value by converting the second value from the analog ALU to a digital value using an analog to digital (A/D) converter. The method may also include storing the second converted value in a digital ALU and processing the second converted value using the digital ALU. In certain aspects, said digital ALU comprises one or more registers and said analog ALU comprises one or more registers. In certain aspects, at least one of said converting and storing comprises use of an exchange register.

In certain aspects, the method further includes adjusting a magnitude of an analog value with an automatic gain control and normalizing a digital value with a shifter. In certain aspects, the values are adjusted to a maximum range of corresponding analog and digital representations in associated memories.

According to some embodiments, a method for synchronizing a digital data word and an analog data word is described. This method may include, for instance, converting a first digital value of a word to a first analog value of a word or a second analog value of a word to a second digital value of a word, and then updating a flag register to indicate that values have been converted. In certain aspects, the converting is performed based at least in part on a determination that an analog or digital representation is missing or that at least one of the first digital value or the second analog value is wrong or erased.

According to some embodiments, a method for performing floating point operations using a mixed signal computer is described. They may be, for instance, using a mixed signal computer or components as described above. The method may begin with reading a first floating point value and a second floating point value from a digital and analog memory of a mixed signal processor using a digital ALU and an analog ALU of the mixed signal processor, wherein the first floating point value comprises a first mantissa and a first exponent and the second floating point value comprises a second mantissa and a second exponent, the first and second mantissa is stored in an analog format in the analog memory, and the first and second exponent is stored in a digital format in the digital memory. The method may further include processing the first and second floating point value using the digital ALU and analog ALU to create a new floating point value comprising a third mantissa and a third exponent based on the processing. In some aspects, the method includes storing the new floating point value in registers associated with the digital and analog ALUs, wherein the third mantissa is stored in the analog format in the analog memory and the third exponent is stored in the digital format in the digital memory.

In some embodiments, the present disclosure relates to a Mixed Signal Computer Architecture that combines the analog and digital domains into one processor. According to aspects of the disclosure, the best advantages of both the digital and analog ALUs can be used. For example, and according to some embodiments, ultra-high performance, analog computing elements can be used for aspects where raw performance is more important than accuracy. But when accuracy is vital, digital computing elements can be used. Where ultra-low power dissipation is a must, once again analog computing elements could be used. The control of the data paths and the ability to program the processing elements may be done by digital control means. However, in some embodiments, analog control may also be used in the MSCA. That is, the control unit may be an analog control unit, or the control unit may be a digital control unit.

In some examples, the MSCA architecture comprises: a digital ALU, an analog ALU, a control unit, two memory arrays, one for digital and one for analog; and, two input and two output busses for digital and analog. In addition, a development environment using a written language may be used. According to certain aspects, a patch panel may not be needed to program the analog ALU.

These and other features of the invention will become apparent to those skilled in the art from the following detailed description, taken together with the accompanying drawings.

BRIEF DESCRIPTION OF THE DRAWINGS

FIGS. 12A-12F depict sets of instructions for a mixed signal ALU according to some embodiments.

DETAILED DESCRIPTION

Figure 1:
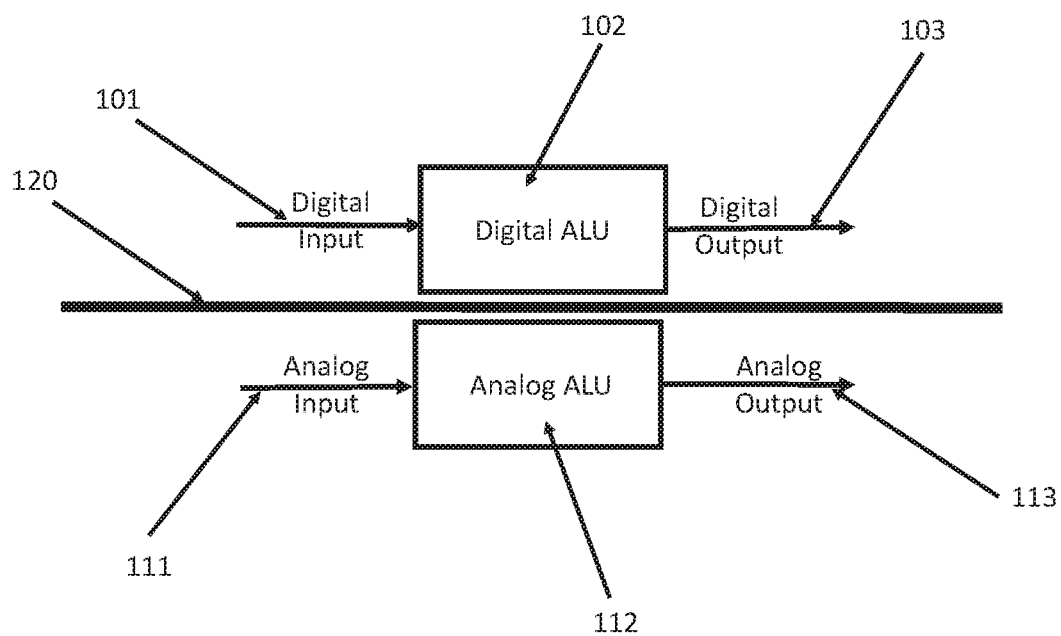
FIG. 1 depicts block diagrams for analog and digital Arithmetic Logic Units.

The present disclosure recognizes that new opportunities are emerging in areas such as neural networks, the Internet of Things (IoT), cloud computing, and image understanding that are demanding the capability of both analog computing elements and digital computing elements.

The limits of digital processing are being approached in multiple aspects. Raw performance is nearing its practical limits. One purported solution has been to take sophisticated digital processing architectures and populate many of them on one semiconductor substrate, giving multi-core processing capability. But even with multi-core Systems on a Chip (SoC) computing elements, the performance demands of many new emerging market opportunities are not being met. At the same time, the power consumption of these high performance digital processing elements is exceeding the ability for the system they are in to power them and cool them. Further, the cost of these high performance digital processing elements is no longer affordable for many applications.

That is where the analog computing elements begin to shine when considered for these many new emerging opportunities. In many applications, the key to the raw performance of a computer is the math unit and particularly the multiplier. In the mid-1970s, the hardware multiplier was introduced to the microprocessor. In doing so, it began the Digital Signal Processing era for the semiconductor industry. It became the defining item of the raw performance of the ALU. In simple terms, the multiplier in a digital computer requires on the order of 10s of thousands of transistors. While in the analog domain, a multiplier may only require 1 to 10 transistors. In terms of raw performance, this means the analog multiplier can perform a multiply in a few gate delays rather than thousands of gate delays in its digital equivalent. Thus the analog multiply can be several of orders of magnitude faster than a digital multiply. At the same time due to its need for fewer transistors, its power dissipation is several orders of magnitude lower than its digital equivalent. The same relationship exists when comparing the cost of the two multipliers.

According to some embodiments, Neural Networks can apply the concept of utilizing a mixed signal function. For example, a neural network may be executed using analog processing, but the final results may be based on a digital evaluation of the analog results. As another example, in a face recognition algorithm, an analog processor may determine the edges and features while the digital processor determines the identity of the face. In some embodiments, certain signals may be processed in the analog domain. For example, RF can be processed in analog before being translated down to baseband where they are converted to digital for further processing. However, when compared to the digital computer, several issues continue to face the analog computer: its analog memory; its programmability; its accuracy; and its use of continuous data versus sampled data.

In the digital world, memories are typically binary, or in powers of two. This makes sense for storing information, keeping the information for long periods of time, and protecting against accumulating noise. Analog memories, on the other hand can have non-linear effects on the data that are being stored, can be poor at long term storage, and be susceptible to corruption by noise.

Historically analog computers have been programmed by using a patch panel. It is not typical to have a written language used to program them. So for analog computers to be programmed they must typically have the necessary functional elements hard wired together either in a permanent fashion, by use of programmable gates, or by a patch panel, which can be used to program an analogy computer. This is in contrast to the ease with which a digital computer processor is programmed, even though typically fixably interconnected with other components, using such things as high level languages, compilers, instruction sets, simulators and emulators. These readily available tools make the process of programming, debugging and modifying the use of a digital computer easy and generally more reliable than the techniques used to program an analog computer.

Accuracy is one of the big issues with which an analog processing element or computer can have issues. In contrast, digital computers have gone from 8 bit to 16 bit to 32 bit and finally to at least 64 bit data words. When comparing the 64 bit floating point accuracy and dynamic range of a digital computer to the 6 to 8 bit accuracy of an analog computer, the conclusion is that there is no place for analog computing elements in today's world.

Aspects of the present disclosure can provide a mixed signal computer that utilizes the strengths of both analog and digital computers.

Referring now to FIG. 1, a present state of the art of computer/processor technology for mathematics units in computers is depicted. As shown in FIG. 1, there are two basic options available in conventional mathematics units. The first option comprises digital processing elements combined into a digital Arithmetic Logic Unit (ALU) 102 with a digital input 101 and a digital output 103. The second option includes analog processing elements combined into an analog ALU 112 with an analog input 111 and an analog output 113. There is a separation 120 between the digital ALU 102 and the analog ALU 112 that can only be resolved by converting the digital input and output to analog or converting the analog input and output to digital.

Figure 2:
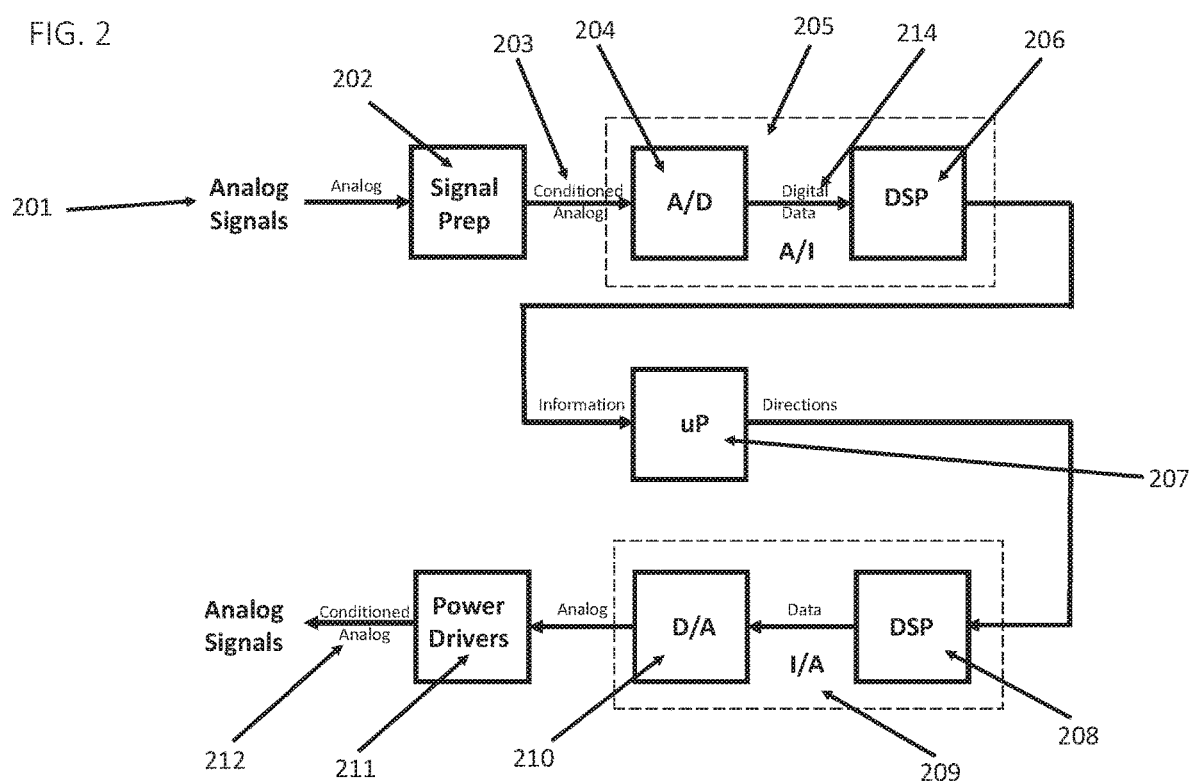
FIG. 2 depicts a block diagram of a digital processor being used with an analog input and analog output.

FIG. 2 depicts how an analog signal 201 may be digitally processed. The analog signal 201 is first prepared for further processing 202 to create a conditioned analog signal 203 that is then introduced to an analog to digital (A/D converter) 204. In some instances, the analog signal preparation involves filtering and other signal conditioning necessary to make the analog signal a conditioned analog signal 203 suitable for further processing. Once the analog signal is converted to digital data 205, the digital data is processed by a digital signal processor (DSP) 206. The combination of the A/D converter 204 and the DSP 206 comprise an analog to information (A/I) converter 214. Once the signal is converted to a digital format as digital information by the A/I converter 214, a microprocessor (uP) 207 makes appropriate decisions and inferences using the information. The output(s) of the uP 207 may comprise directives for the information to an analog I/A converter 209. The I/A converter comprises a digital signal processor 208 and a digital to analog converter 210. The output from the I/A converter may be an appropriate analog signal which the power driver 211 properly conditions and the conditioned signal 212 is then used to control and/or drive the appropriate functional units.

Figure 3:
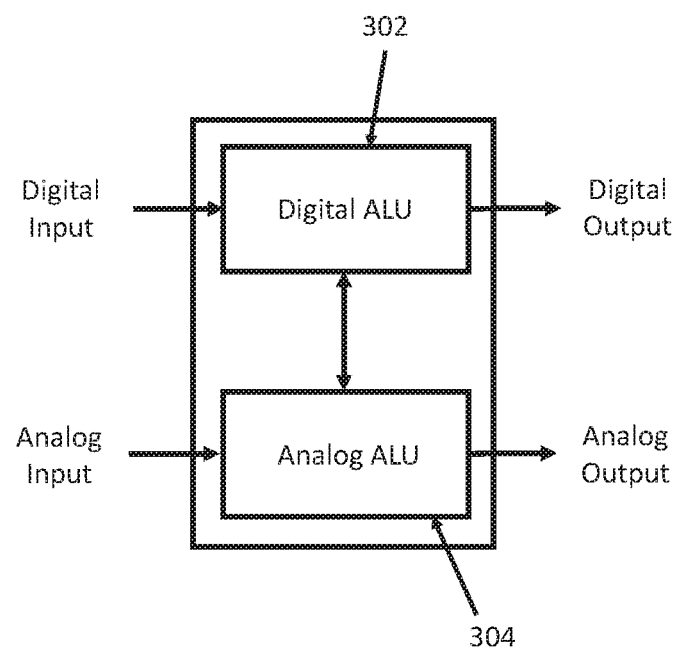
FIG. 3 depicts a connected Digital ALU and Analog ALU with respective inputs and outputs system in accordance with exemplary embodiments.

FIG. 3 depicts a digital ALU 302 in connection with an analog ALU 304 with respective inputs and outputs according to some embodiments. In some respects, digital signal processing is based on a clock and sampled data from which all information is derived. Accordingly, signals may be sampled using a sample clock, where the sample clock is determined based on the signal content and a system clock. In some embodiments, the digital ALU 302 mathematically manipulates the signal within each sample period based on a sequence of instructions from a control unit. The signals, such as data, are stored in registers and provided to the digital ALU 302 at the appropriate times and in the appropriate sequence such that the digital ALU 302 may manipulate them correctly.

In some respects, analog signal processing does not require a clock and may run continuously. In some embodiments, the analog ALU 304 may operate in both a discrete mode and a continuous mode. In the discrete mode, the analog ALU 304 operates based on sampled data and clocked instruction sequences (similar to the operation of the digital ALU 302). The analog ALU 304 is used in the discrete mode, for example, when reduced power dissipation is more important than data accuracy on sampled data or when performance in higher speed than the digital ALU 302 is needed. In the continuous mode, the analog ALU 304 receives a continuous analog signal and manipulates the analog signal using solid state analog switches to properly connect processing elements based on predetermined instructions. The analog ALU 304 is used in the continuous mode, for example, with signals that are processed as continuous, non-sampled inputs.

In some embodiments, discretely continuous processing may refer to processing time segments of a continuous signal. In some embodiments, discretely continuous may comprise a signal sample for a short time period during a larger time period. In other embodiments, discretely continuous may comprise processing a sample of a continuous signal rather than continuously processing the signal. For example, discretely continuous processing may comprise processing a one second segment of a continuous signal every ten minutes. According to some embodiments, a Mixed Signal Computer Architecture (MSCA) as described herein enables such discretely continuous processing. In an embodiment, the MSCA comprises two simultaneous input threads where one is discrete and the other is continuous, but both under synchronized control. In some embodiments, the MSCA comprises one digital ALU with multiple analog ALUs in the same architecture, multiple digital ALUs and analog ALUs in the same architecture, or one analog ALU with multiple digital ALUs in the same architecture.

In some embodiments, the analog ALU 304 provides higher raw performance, lower power dissipation, less accuracy, and more additive noise compared to the digital ALU 302. In some embodiments, the digital ALU 302 provides more accuracy, less noise once captured, more linearity, slower processing, and higher power dissipation compared to the analog ALU 304. The data types required for the digital ALU 302 and the analog ALU 304 may be different and the respective outputs may not be compatible without additional manipulation.

In some embodiments, an analog multiply requires a few transistors and can be accomplished in picoseconds. In contrast, a digital multiply requires thousands of transistors and can be accomplished in nanoseconds. The difference in processing for analog multiply and digital multiply amounts to about three orders of magnitude in difference (about 1,000 times) in multiply accumulate cycles. Not only are the speeds different, but the analog multiply and the digital multiply may also be asynchronous to each other (also referred to as latency). The latency of the analog ALU is not only different, but variable. Due to the faster performance of the analog multiply, the analog ALU will have far less delay from the signal input to the signal output than in the digital ALU.

Figure 4:
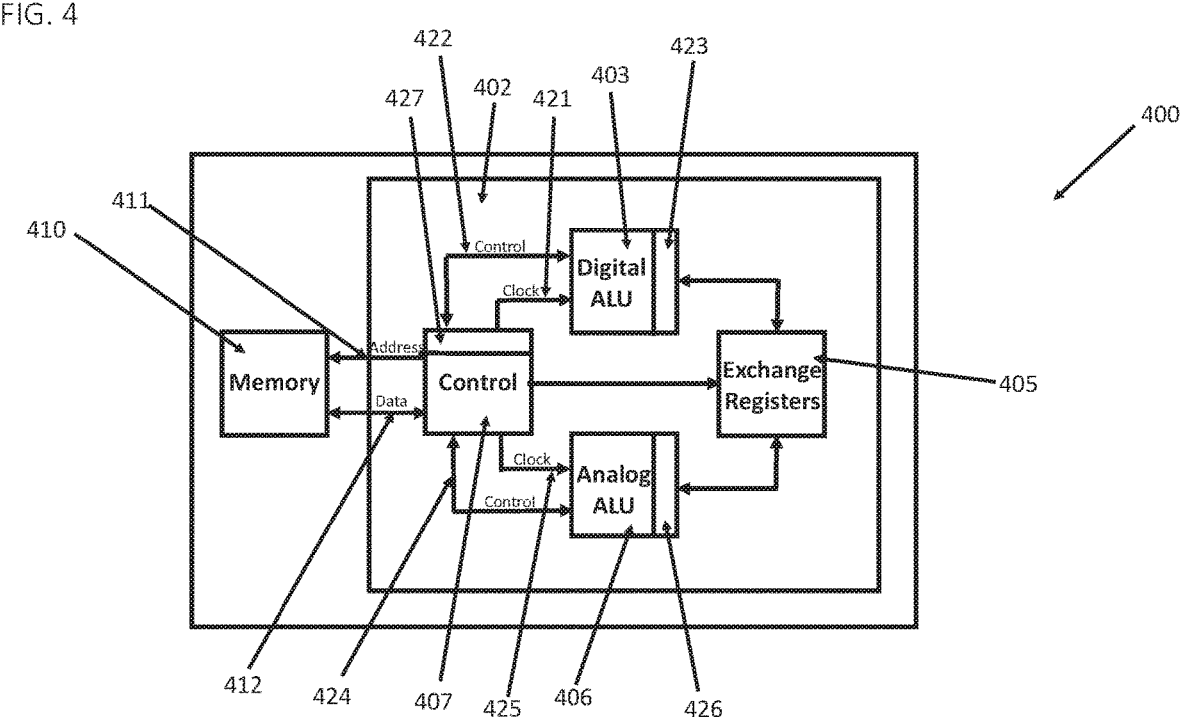
FIG. 4 depicts a simplified block diagram of one embodiment for a Mixed Signal Computer Architecture.
Figure 5:
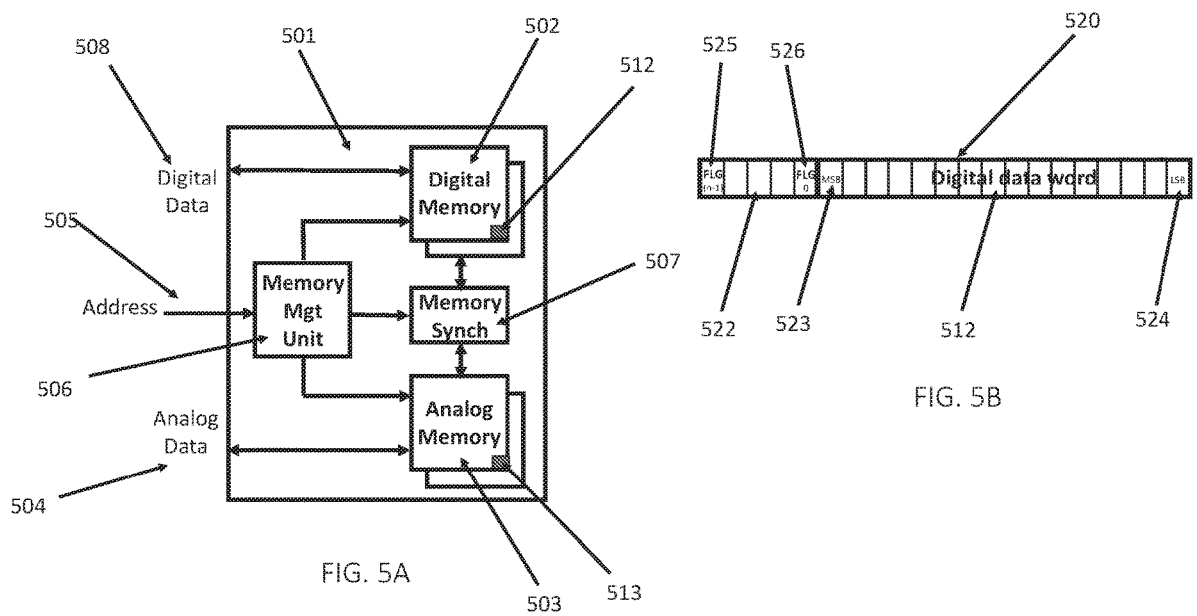
FIGS. 5A-5B depict a mixed signal memory system according to embodiments.

FIG. 4 depicts one embodiment of a Mixed Signal Computer Architecture (MSCA) 400 of the present disclosure. As shown in FIG. 4, the MSCA 400 comprises a mixed signal processor 402 and associated memory 410. The associated memory 410 is described in further detail with respect to FIG. 5. In some embodiments, the mixed signal processor 402 comprises two ALUs: a first digital ALU 403 and a first analog ALU 406. Each of the ALUs 403, 406 comprises a separate register file 423 and 426, respectively, in this example. In some embodiments, the mixed signal processor 402 may comprise more than one of each type of ALU and depending on the data to be analyzed and/or processed. In some embodiments, the mixed signal processor 402 may comprise one type of ALU and multiple versions of the opposite type of ALU (e.g. one digital ALU 403 and many analog ALUs 406, or vice versa). The mixed signal processor 402 further comprises an exchange register 405 to convert digital data to analog data and analog data to digital data, when appropriate, such that the two ALUs 403, 406 can work with a same set of data. All of the elements in the mixed signal processor 402 may be under the control of a control unit 407. In an embodiment, the control unit 407 comprises a digital control unit. In other embodiments, the control unit 407 comprises an analog control unit, or both the analog control unit and the digital control unit. The control unit 407 manages the data from the memory 410 by use of the address 411 and data 412 lines.

Figure 6:
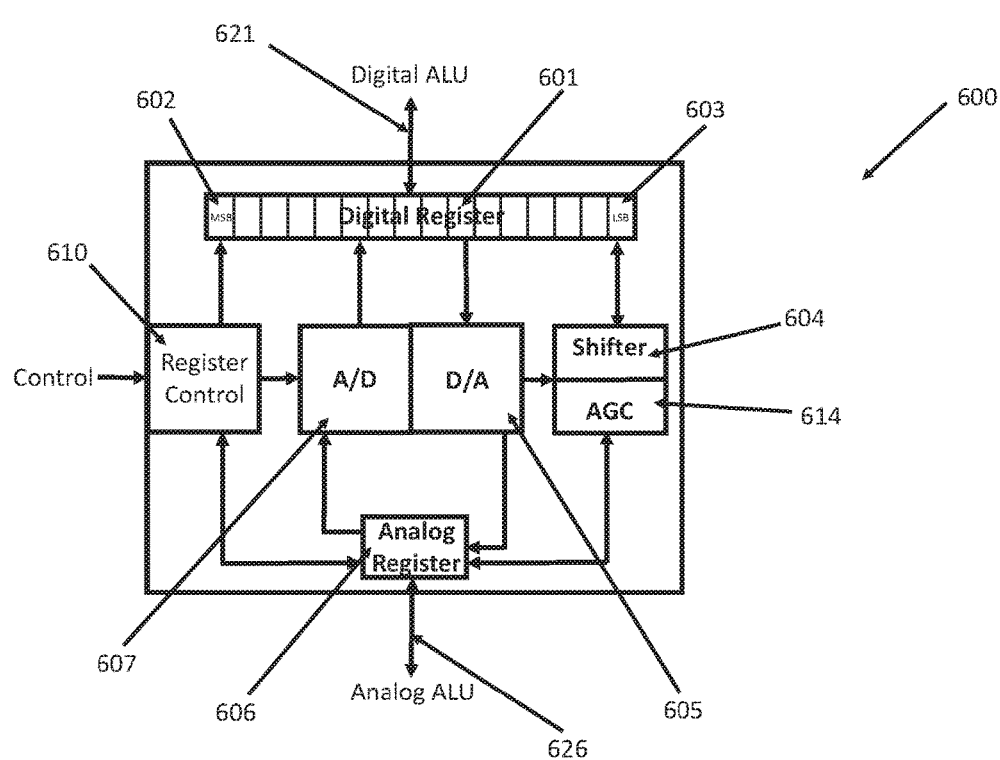
FIG. 6 depicts an exchange register according to some embodiments.

The exchange registers 405, which are described in further detail with respect to FIG. 6, in the MSCA 400 allow for analog data from the analog ALU 406 to be transformed to digital data for use by the digital ALU 403, and digital data from the digital ALU 403 to be transformed to analog data for the analog ALU 406. In some embodiments, the registers 423, 426 in the two ALUs 403, 406 may be part of the ALUs, as shown in FIG. 4. In some embodiments, one or more of the registers 423, 426 may be comprised in the exchange register 405. A set of instructions stored in a memory 427 is used by the control unit 407 to manage the exchange register(s), memories and perform the appropriate handshaking between the digital ALU 403 and the analog ALU 406.

The exchange registers 405 may be synchronized to be seamless for both the analog and digital ALUs registers 426, 423. Accordingly, in some embodiments, any exchanged data using the exchange registers 405 appears to happen in real time. Because of the two types of ALUs and memories, and exchange register, the instruction set for the MSCA 400 (exemplary instructions further shown in FIGS. 12A-12F) may be more extensive than a digital computer instruction set, but otherwise analogous to the digital computer instruction set. In a similar manner, a development environment similar to that of a digital computer may be used to handle the analog ALU 406, memories and exchange register 405, in addition to the digital ALU 403. In some embodiments, instructions may be provided in addition to the conventional instructions used for the digital ALU 406. Such additional instructions may allow the analog ALU, the exchange registers and any mixed signal instructions to be consistent with the digital ALU instructions according to some embodiments. More particularly, the instruction set for the analog ALU 406 could basically replicate those used by the digital ALU 403. Accordingly, additional instructions are provided to control the analog ALU, exchange registers, memories, and the mode of processing.

When both the digital ALU 406 and the analog ALU 403 are operating in a discrete mode of processing, for instance where both ALUs are using sampled data, the ALUs 403, 406 may use clock inputs 421, 425 as shown in FIG. 4. In some embodiments, the control unit 407 controls the two ALUs 403, 406 using the control lines 422, 424 and appropriate clocks 421, 425 for the two ALUs 403, 406. In some embodiments, the two clock signals 421, 425 may be the same frequency. However, the two clock signals 421, 425 may comprise different frequencies depending on the signals being processed.

When only analog processing is being performed, the analog ALU 406 may function at its optimal speed which may be continuous or discrete, and the digital ALU 403 may be idle according to some embodiments. When only digital processing is being performed, the digital ALU 403 may function at its optimal speed, and the analog ALU 406 may be idle according to some embodiments. In the mixed signal processing mode both the analog and digital ALUs 406, 403, respectively, may run at their respective optimal speeds, and are synchronized with each other as necessary.

In some embodiments, the two ALUs 403, 406 may be synchronized to maximize performance while minimizing power dissipation. As a non-limiting example, the two ALUs may perform independently until a specific synchronization is needed. Such specific synchronization may be based on a time element from the system clock, sample clock or counter or based on an event such as an interrupt, threshold or instruction.

FIG. 5A depicts one embodiment of a mixed signal buffered I/O memory system 501, and may be arranged as memory 410 in FIG. 4. The mixed signal buffered I/O memory system comprises digital memory arrays 502 and analog memory arrays 503. In some embodiments, a memory management unit 506 controls the mixed signal memory system 501 using an address bus 505, an analog data bus 504, and a digital data bus 508. As shown in FIG. 5A, the internal address bus 505 is connected to both the digital memory array 502 and the analog memory array 503 via the memory management unit 506. Accordingly, a same data point is stored in both arrays 502, 503 each with its appropriate information. For example, the data point may comprise digital data and analog data, where the digital data comprises an exponent stored in the digital memory arrays 502 and the analog data comprises a mantissa of a floating point representation stored in the analog memory arrays 503. As shown in FIG. 5B, a representative digital word 520 (also referred to as a digital representation) is stored in a portion of memory 512 which is a part of the digital memory array 502 according to some embodiments. In some embodiments, the digital memory array 502 contains the digital word 520 comprising a most significant bit 523, a least significant bit 524 and n-2 bits between, as shown in FIG. 5B, where n indicates a number of bits in the digital word 520. As shown in FIG. 5B, the digital memory array 502 may also contain an array of flag bits 522. In some embodiments, the flag bits 522 may comprise one or more bits from FLG (0) 526 to FLG (n-1) 525. In some embodiments, the analog data representation in a portion of memory 513 (which is part of memory 503) may or may not be physically collocated with the digital representation 512, depending on the physical design of the memory system.

In some embodiments of the mixed signal memory system 410, the address for the location of a same data value or point in both the digital memory array 502 and the analog memory array 503 is the same for their corresponding memory array. Accordingly, when the control unit of the mixed signal computer sends the address for the common data point, both analog and digital representations from the analog memory array 503 and the digital memory array 502, respectively, are returned to the ALU control unit 407 and put into the appropriate registers 423, 426. If one of the two representations, either the digital representation 512 or the analog representation 513, is not available, a memory synchronization register 507 creates the missing data from the representation that is available under the direction of the memory management unit (MMU) 506 where a flag is set in the flag bits 522 of the memory to indicate which one of the two representations is the original source for the data according to some embodiments. If the two memory representations of the common data value are not the same, the memory management unit 506 will determine which representation is correct based on the most recently used representation, the original data point or the neighboring data points. The other representation deemed incorrect will be re-created and a flag will be set in flag memory to indicate the recreation.

In some embodiments, synchronization of memory representations 512, 513 between the two memory arrays 502, 503 may be used. For example, when a digital word is written to the digital memory array 502, the digital word may be immediately converted to analog and stored in the associated analog memory array 503. Similarly, when an analog word is written to the analog memory array 503, the analog word may be immediately converted to digital and stored in the associated digital memory array 503. In some embodiments, the digital and analog memory arrays 502, 503 may not be synchronized and treated as separate memory arrays. When the digital and analog memory arrays 502, 503 are determined not to be synchronized, a synchronization instruction may be utilized to configure both the analog and digital arrays to properly portray the same data point. In some embodiments, digital converted to analog data or analog converted to digital data may be stored and each memory location comprises a flag to determine which of the two (analog or digital) memories had the data to be transferred to the other. In some embodiments, the converted data may be one data word, a block of data words or the whole memory bank.

Maintaining the same data point in the digital memory array 502 and the analog memory array 503 portrayed in two different ways can provide certain advantages. For instance, the analog memory array 503 may have a tendency to drift. The corresponding digital memory array 502 may then be used as the correct data and the analog memory array 503 may be refreshed based on the correct data stored in the corresponding digital memory array 502. When the digital memory array 502 and the analog memory 503 are operating independently, selective synchronization may be necessary. In some embodiments, the analog memory array 503 may require self-refresh. In such embodiments, the charge on the memory cell may be detected and re-applied on a periodic basis.

In some embodiments of the MSCA 400, some digital and analog memory locations may not be the same and may be used independently by the two ALUs. In some embodiments, a mixed signal instruction may utilize a mixed signal floating point representation for data using portions of each of the two different memory arrays. One such floating point arrangement may be where the mantissa is stored in analog format in the analog memory array 503 and the exponent is stored in digital format in the digital memory array 502. In such instances, the MMU 506 may direct the two memory arrays 502, 503 and the memory synchronization register 507 to store the floating point representation. MSCA instructions directed to storing the floating point representation is described further with respect to FIGS. 12A-12F.

FIG. 6 depicts one embodiment of an exchange register 600. In some embodiments, the exchange register 600 comprises a digital register 601 containing a digital data word with a most significant bit (MSB) 602 and a least significant bit (LSB) 603, and an analog register 606. For simplicity, only one digital and analog register location is shown in FIG. 6, but there may be an array of locations in alternative embodiments. The interface between the digital register 601 and the analog register 606 may comprise multiple data conversion units. As shown in FIG. 6, the interface comprises analog to digital converter 607 to convert a datum stored in the analog register 606 and store the converted datum in the digital register 601, a digital to analog converter 605 to convert a datum stored in the digital register 601 and store the converted datum in the analog register 606, an automatic gain control (AGC) circuit 614 and a digital shift apparatus 604. The functional elements of the exchange register 600, such as the digital register 601, the digital shift apparatus 604, the digital to analog converter 605, the analog register 606, the analog to digital converter 607, and the automatic gain control circuit 614 are controlled by a register controller 610 which in turn is controlled by the mixed signal ALU control unit 407.

In some embodiments, when instructed by the ALU's control unit 407, the exchange register 600 may read the value from a specified digital ALUs register 423 and immediately convert the digital result 621, now in the exchange register's digital register 601, to an analog value using the D/A converter 605 and store it in the analog register 606 ready to be written 626 to a specified analog ALU register 426. In some embodiments, when instructed by the ALU's control unit 407, the exchange register 600 may read the value from a specified analog ALU register 426 and convert the analog result 626, now in the exchange register's analog register 606, to a digital result using the A/D converter 607 and store it in the digital register 601 ready to be written 621 to a specified digital ALU register 423.

Both analog and digital accuracy may be managed by the register control unit 610. On the analog side, the use of the Automatic Gain Control (AGC) circuit 614 may be used to maintain full range of the analog signal according to some embodiments. On the digital side, the use of a shifter 604 may be used to maintain full range of the digital data word according to some embodiments. In some embodiments, the AGC circuit 614 and the shifter 604 are both controlled by the register control unit 610.

In some embodiments, the analog register 606 may comprise an analog memory cell including a floating gate transistor or capacitor and may be configured to: put a charge on the cell associated with the value of an analog signal, calibrate the cell when appropriate, and configure the AGC circuit 614 to assure full use of the register cells range. If the AGC circuit 614 is used, it needs to be synchronized with the shifter 604 on the digital memory or digital register 601 according to some embodiments. The digital and analog memories/registers may be synchronized by the digital representation of the data which reflects the data value in relationship to the other stored data values in the data set. That is, the digital representation is a combination of the analog representation as altered by the AGC circuit 614 according to some embodiments. Alternatively, the digital and analog memories/registers may be synchronized through the use of the digital data word as the equivalent exponent of the AGC circuit 614. Accordingly, the combined digital and analog memory may comprise a floating point representation. For example, the analog memory being the mantissa and the digital memory being the exponent based on the AGC circuit 614 value. The number of cells needed in the analog register may depend on the operation of the analog ALU and the number of inputs.

In some embodiments, the exchange register 600 acts as a mailbox where a digital representation 621 is placed in the digital side and an analog representation 626 of the same data is available on the analog side of the register. Similarly, the exchange register 600 may act as a mailbox where an analog representation 626 is placed in the analog side and a digital representation 621 of the same data is available on the digital side of the register. In an embodiment, the digital and analog representations are synchronized, unless otherwise directed by the register control unit 610.

In some embodiments, the exchange register 600 may be part of the analog ALU register 426 and/or the digital ALU register 423, but is shown in FIG. 6 as a stand-alone register which is controlled by the mixed signal processor control unit 407 and the exchange register controller 610 according to some embodiments. In some embodiments, special instructions may be used to control the exchange register 600.

In some embodiments, mixed signal processor 402 may comprise as many as three sets of registers. More specifically, the mixed signal process 402 may comprise one set digital registers 423, one set analog registers 426, and one set exchange registers 405, 600.

Figure 7:
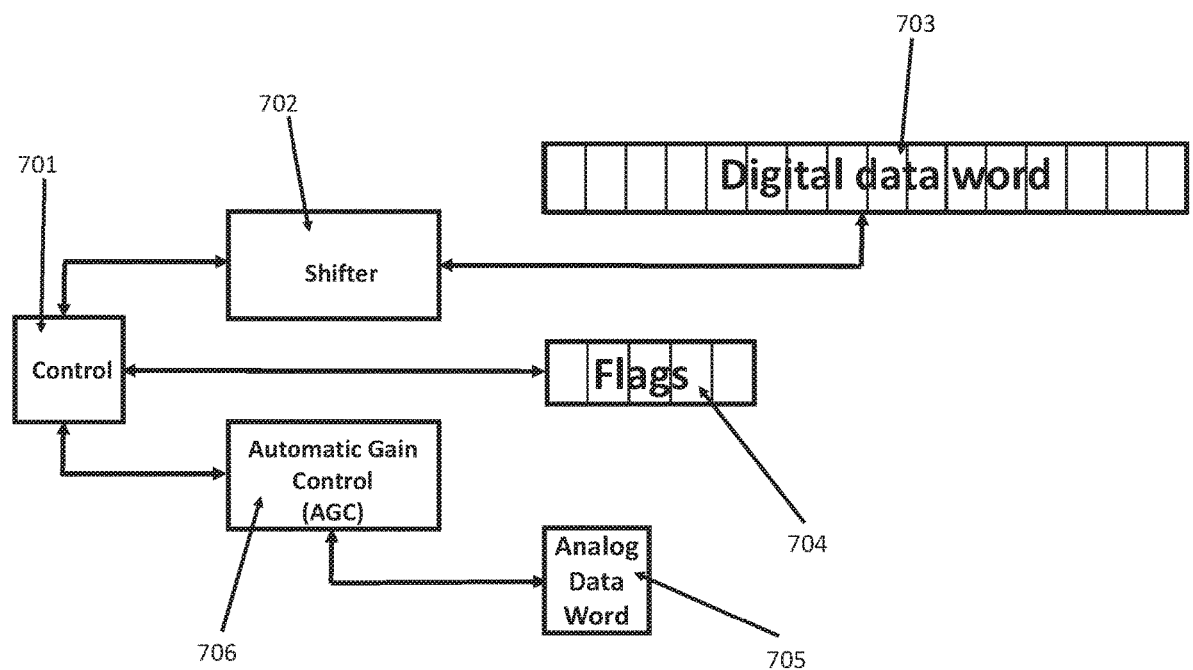
FIG. 7 depicts an embodiment for adjusting values stored in the digital and analog memory.

FIG. 7 depicts one embodiment of storing a data word in its two forms, digital 703 and analog 705. Under the management of a controller 701 (also referred to as memory management unit 506 in FIG. 5A) the analog form and the digital form of the data word may be adjusted to maximize the range of both memories. In some embodiments, an automatic gain control circuit 706 may increase or decrease the magnitude of the value stored in the analog memory 705 while a shifter 702 may be used to normalize the digital representation of the data in the data memory 703. In some embodiments, the controller 701 may use the flag register 704 to keep information about the data word and its initial origin.

Figure 8:
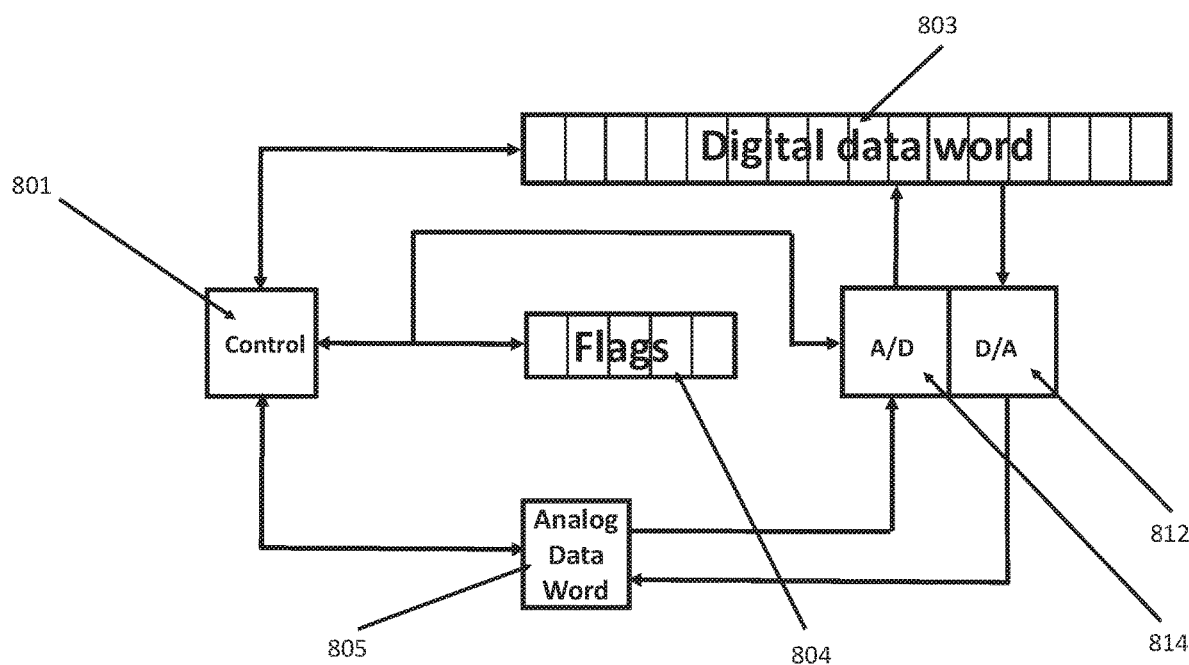
FIG. 8 depicts an embodiment for converting values stored in digital and analog memory.

FIG. 8 depicts one embodiment for synchronizing a digital data word 803 and an analog data word 805. In some embodiments, a controller 801 (also referred to as the memory synchronization register 507) may control an A/D converter 814 and a D/A converter 812 to convert the digital value of a particular data stored in a digital data word 803 to form an analog value to be stored as an analog data word 805. In some embodiments, the controller 801 may control the A/D converter 814 and the D/A converter to convert the digital value to form the analog value or convert the analog value to form the digital value when an analog or digital representation is missing or when one of the two representations is determined to be incorrect or erased. A flag register 804 may be used to establish which of the two representations has been altered or updated.

Figure 9:
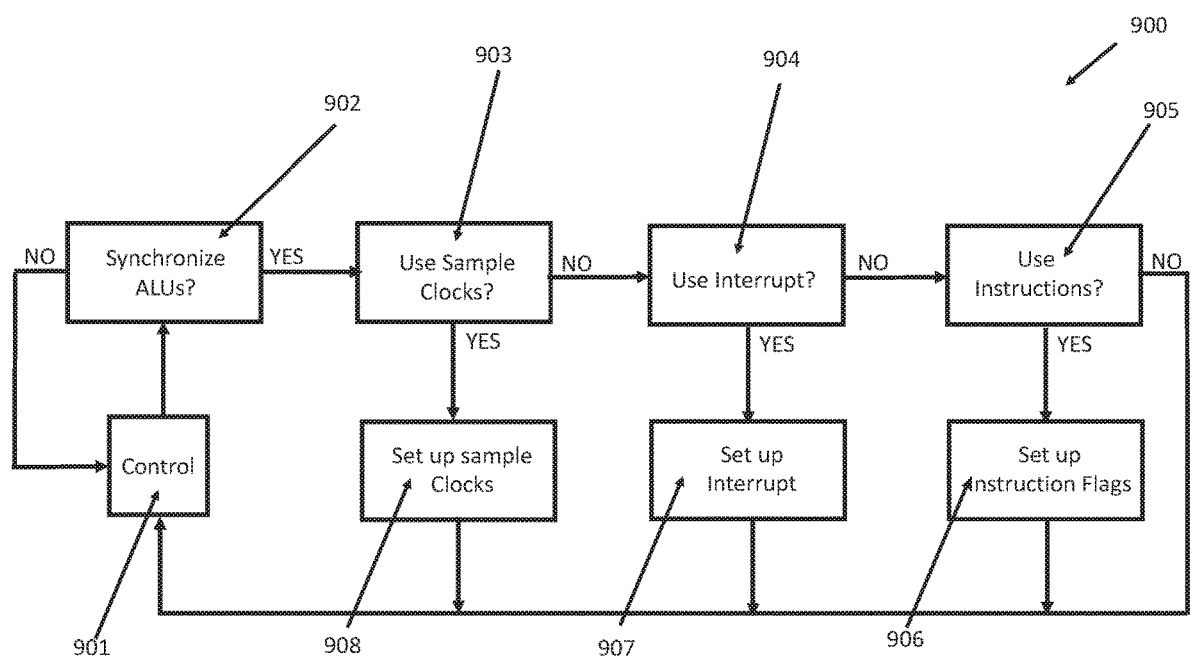
FIG. 9 depicts an embodiment for selective synchronization of analog and digital memories.

FIG. 9 depicts one embodiment of how the analog ALU 406 and the digital ALU 403 may be synchronized. In some embodiments, the two ALUs, depending on which operating mode they have been set up in, may be operating in a synchronized mode with both ALUs using the same clock. In some embodiments, the two ALUs may be operating in a non-synchronized mode processing sampled data with two separate clocks. In some other embodiments, the two ALUS may be operating in an arrangement where the analog ALU 406 is in continuous mode without a clock and where the digital ALU 403 either is using a clock or is halted. In any of these three embodiments, a process 900 shown in FIG. 9 may be initiated in step 901 with an instruction to synchronize the ALUs. In step 902, a determination by the mixed signal processor control unit 407, based on the set of instructions stored in the memory 427, to synchronize memories may begin a process of determining in which of the processing modes the synchronization request occurs. As shown in FIG. 9, a YES in response to each of the three queries in steps 903, 904 and 905, sets up the desired synchronization method 908, 907 or 906, respectively, for the ALUs according to some embodiments. In step 903, the mixed signal processor control unit 407 determines whether sample clocks may be used. If the mixed signal processor control unit 407 determines that sample clocks may be used, the process 900 proceeds to step 908 in which the mixed signal processor control unit 407 sets up sample clocks. If the mixed signal processor control unit 407 determines that sample clocks may not be used, the process 900 proceeds to step 904 in which the mixed signal processor control unit 407 determines whether interrupt may be used. If the mixed signal processor control unit 407 determines that interrupt may be used, the process 900 proceeds to step 907 in which the mixed signal processer control unit 407 sets up the interrupt. If the mixed signal processor control unit 407 determines that interrupt may not be used, the process 900 proceeds to step 905 in which the mixed signal processer control unit 407 determines whether instructions may be used. If the mixed signal processer control unit 407 determines that instructions may be used, the process 900 proceeds to step 906 in which the mixed signal processer control unit 407 sets up instructions flags. If the mixed signal processer control unit 407 determines that instructions may not be used, the process 900 concludes with no set up alterations.

Figure 10:
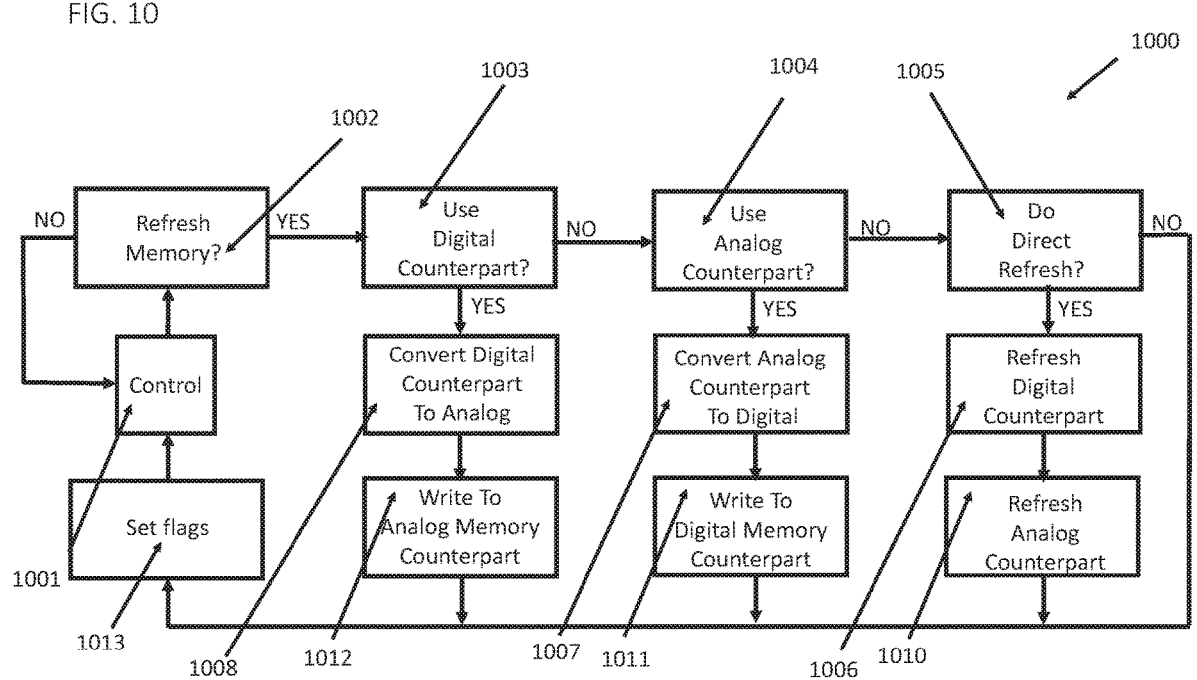
FIG. 10 depicts an embodiment for refreshing analog memory.

FIG. 10 depicts one embodiment of a process 1000 performed by the memory management unit (MMU) 506 to refresh a memory. The process 1000 may be initiated with an instruction to refresh the memories. In step 1002, the memory management unit 506 determines whether a memory is to be refreshed. The initial determination made in step 1002 is directed to which type of memory is to be refreshed according to some embodiments. If the memory management unit 506 determines that a memory is to be refreshed, the process 1000 proceeds to step 1003 in which the memory management unit 506 determines whether to use a digital counterpart. If the memory management unit 506 determines to use the digital counterpart, the memory management unit 506 begins the synchronization tasks in steps 1008 and 1012 starting with digital data. For example, the memory management unit 506 converts a digital counterpart data to analog format in step 1008 and writes the converted data to the analog memory. In some embodiments, once the synchronization tasks in steps 1008 and 1012 have been completed, the memory management unit 506 sets the appropriate flags in step 1013. If the memory management unit 506 determines not to use the digital counterpart in step 1003, the process 1000 proceeds to step 1004 in which the memory management unit 506 determines whether to use an analog counterpart. If the memory management unit 506 determines to use the analog counterpart, the memory management unit 506 begins the synchronization tasks in steps 1007 and 1011 starting with analog data. For example, the memory management unit 506 converts an analog counterpart data to digital format in step 1007 and writes the converted data to the digital memory 1011. In some embodiments, once the synchronization tasks in steps 1007 and 1011 have been completed, the memory management unit 506 sets the appropriate flags are set in step 1013. If the memory management unit 506 determines not to use the analog counterpart, the process 1000 proceeds to step 1005 in which the memory management unit 506 determines whether a direct refresh is needed. If the memory management unit 506 determines that the direct refresh is needed, the synchronization tasks in steps 1006 and 1010 are performed by the memory management unit 506. In some embodiments, the memory management unit 506 may perform steps 1006 and 1010 one or more of the two memory types (i.e., the analog memory and the digital memory). For example, the memory management unit 506 refreshes the digital counterpart data in step 1006. As another example, the memory management unit 506 may alternatively or additionally refresh the analog counterpart data in step 1010. In some embodiments, once the synchronization tasks in steps 1006 and 1010 have been completed, the memory management unit 506 sets the appropriate flags in step 1013. If the memory management unit 506 determines that no direct refresh is necessary in step 1005, the process proceeds to step 1013 in which the memory management unit 506 indicates that no refresh has been made and sets the appropriate flags 1013 to indicate that no synchronization tasks were completed. In some embodiments, the memory management unit 506 may receive request for memory refresh of one or both memories from the control unit. In some embodiments, the memory management unit 506 may determine NO in steps 1003, 1004, and 1005, thereby concluding the process 1000 without any changes.

Figure 11:
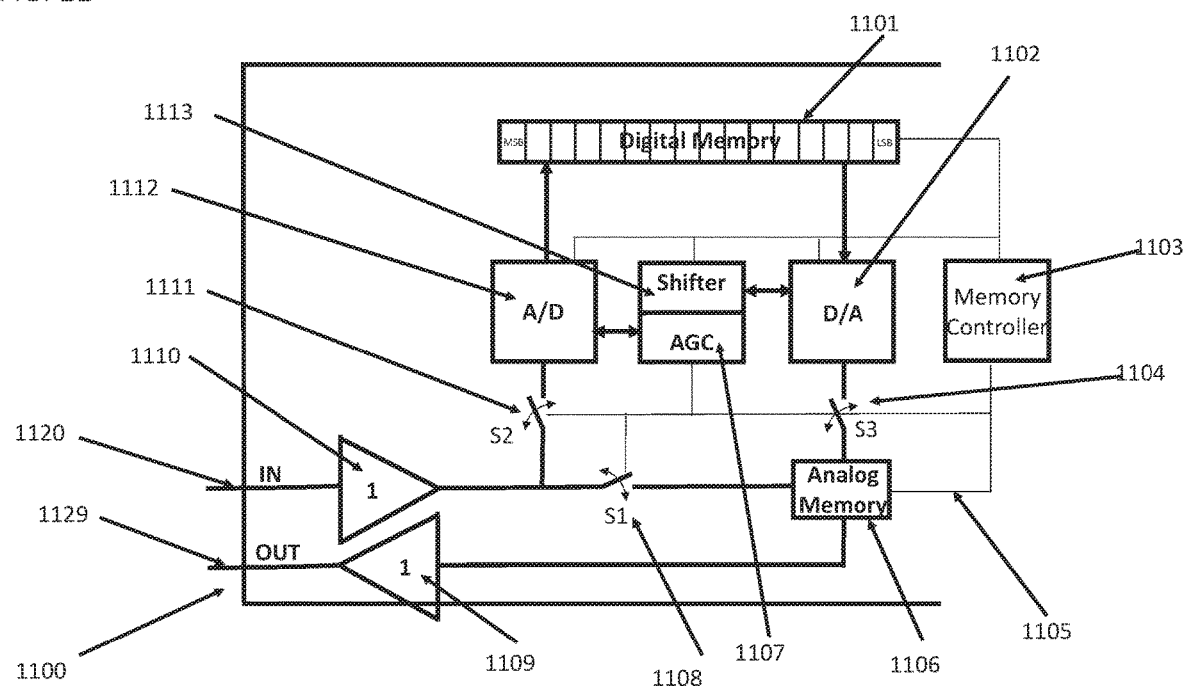
FIG. 11 depicts an embodiment for a memory mapped analog input and output port.

FIG. 11 depicts one embodiment of an analog memory mapped I/O 1100. As shown in FIG. 11, an analog input 1120 is connected to an amplifier 1110 with a gain of 1 in this example. A memory controller 1103 controls a first switch S1 1108 such that the output of the amplifier 1110 (for instance, the input signal) is selectively sent directly to the analog memory 1106 when the first switch S1 1108 is closed according to some embodiments. If a discrete representation of the input is desired, and the memory controller 1103 controls the first switch S1 1108 and a second switch S2 1111 such that the input signal is selectively sent to the A/D converter 1112 when the second switch S2 1111 is closed and the first switch S1 1108 is opened according to some embodiments. In such embodiments, the input signal received as an analog input by the A/D converter 1112 is then converted to its digital representation and stored in the digital memory 1101. In some embodiments, the discrete representation may be stored in the analog memory 1106. In such embodiments, the digital representation is presented to the D/A converter 1102 which is then converted to its analog representation and stored in the analog memory 1106. In some embodiments, the memory controller 1103 may be configured to control a third switch S3 1104 such that the converted analog representation may be stored in the analog memory 1106 when the third switch S3 1104 is closed. In some embodiments, a shifter 1113 (also referred to as shifter 604 in FIG. 6) and an automatic gain control circuit 1107 (also referred to as AGC circuit 614 in FIG. 6) may be used to store either the digital or analog representation at a convenient processing point. In some embodiments, an analog output 1129 comes directly from the analog memory 1106 through an output amplifier 1109 with a gain of 1. All of the options for the memory mapped analog input and output are controlled by the memory controller 1103 through a control bus 1105.

FIGS. 12 A-12F show sets of instructions in tables which may be useful for the analog and digital ALUs described herein and according to some embodiments.

FIG. 12A shows a table 1200 for several arithmetic functions for the ALUs described herein. The instructions in column 1201 comprise multiply 1207, add 1210, subtract 1211 and, divide 1212 functions according to some embodiments. The other columns give a description of the action 1202 the instruction has on the CPU circuitry, the operation code (also referred to as "opcode") for the digital ALU 1203, the opcode for the analog ALU 1204, and the opcodes for mixed signal operations 1205. In some embodiments, there are opcodes for the digital multiply, analog multiply and the two mixed signal multiplies as shown in FIG. 12A for the multiply instructions 1207, 1208 and 1209. In some embodiments, the digital or analog multiply execution 1213 includes taking the data value from a register "a" in the respective digital ALU register set 423 or analog ALU register set 426 and multiplying the data value with the value from a register "b" in the same digital ALU register set 423 or analog ALU register set 426 and then placing the result into a register "c" in the same ALU register set. The two mixed signal operations 1214 and 1215 shown in FIG. 12A perform a similar multiplication, but the 1214 operation instructs the multiply function to occur in the analog ALU register set and storing the result in the digital ALU register set. Similarly, the 1215 operation instructs the multiply function to occur in the digital ALU register set and storing the result in the analog ALU register set.

FIG. 12B shows a table 1220 for several floating point arithmetic functions for the ALUs described herein. In certain embodiments, Floating point arithmetic functions for the ALUs are mixed signal instructions that may utilize a mixed signal floating point representation for data using portions of each of the two different memory arrays. In some embodiments, a floating point arrangement may comprise the mantissa stored in analog format in the analog memory 503 and the exponent stored in digital format in the digital memory 502. In such embodiments, the MMU 506 may direct the two memories 502, 503 and the memory synchronization register 507 to store the floating point representation. More specifically, when referring to the multiplication of two floating point numbers the following actions may occur according to some embodiments. First, the analog mantissas are copied or moved from a stored location in the analog memory 504 and loaded into two registers in the register set 426 of the analog ALU 406. The analog ALU 406 then performs a multiplication and stores the result in a different register in the analog ALU register set 426. Similarly, the exponents for these two mantissas may be copied or moved from a stored location in the digital memory 502 and loaded into two registers in the register set 423 of the digital ALU 403. The digital ALU then adds the two exponents and stores the result in a different register in the digital ALU register set 423. The resulting values for the exponent and mantissa may then be used for other purposes or temporarily stored in the respective register sets of the ALUs, or moved to their respective memory locations. Other representative examples for mixed signal instructions are shown in table 1220 of FIG. 12B.

FIG. 12C shows a table 1230 presenting examples of analog instructions useful for the mixed signal processor 402 using the same table format of table 1200 of FIG. 12A.

FIG. 12D shows a table 1240 presenting examples of the exchange register 405 instructions useful for the mixed signal processor 402 using the same table format of table 1200 of FIG. 12A.

Figure 12E:
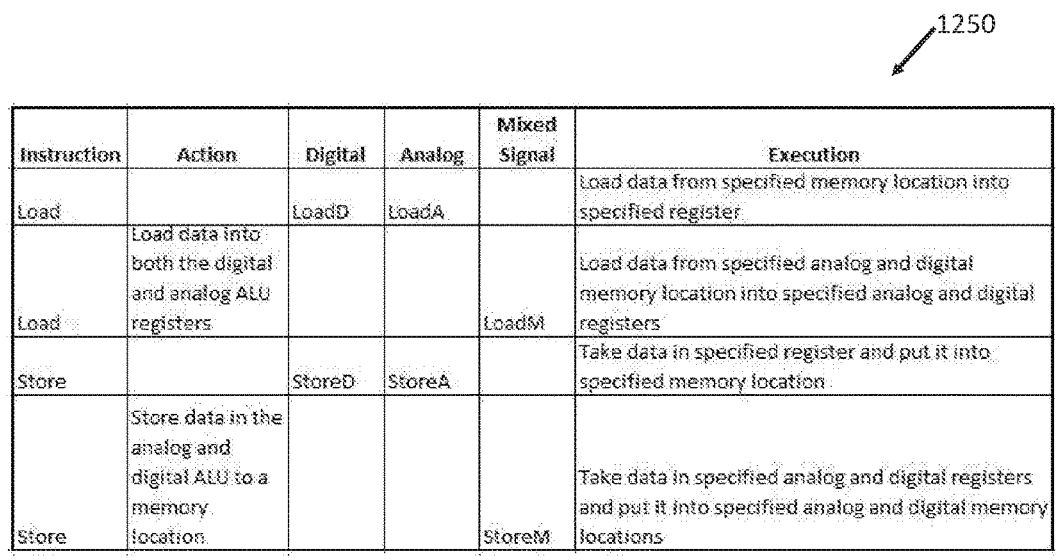

FIG. 12E shows a table 1250 presenting examples of memory operations useful for the mixed signal processor 402 using the same table format of table 1200 shown in FIG. 12A.

Figure 12F:
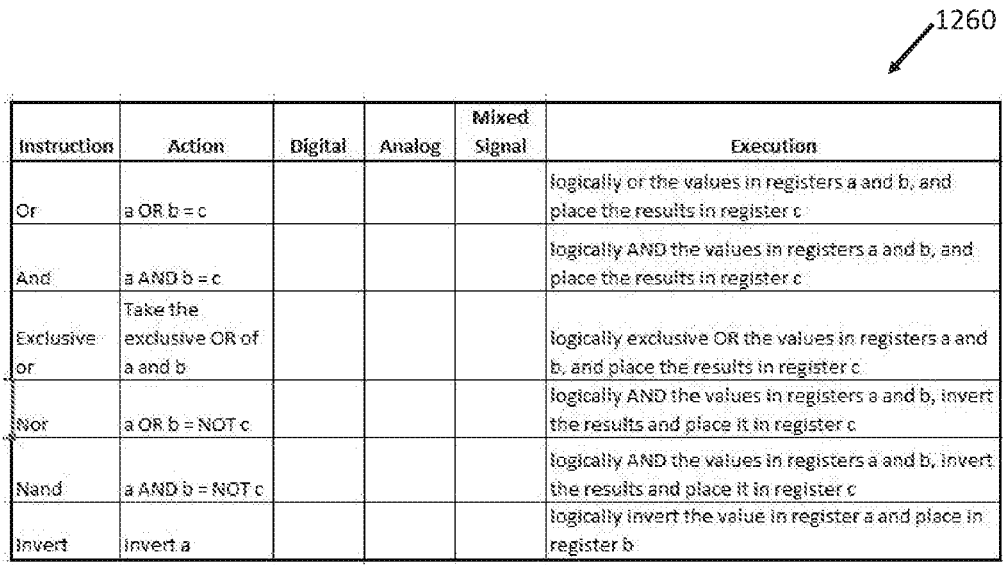

FIG. 12F shows a table 1260 presenting examples of logic instructions useful for the mixed signal processor 402 using the same table format of table 1200 shown in FIG. 12A.

Figure 13:
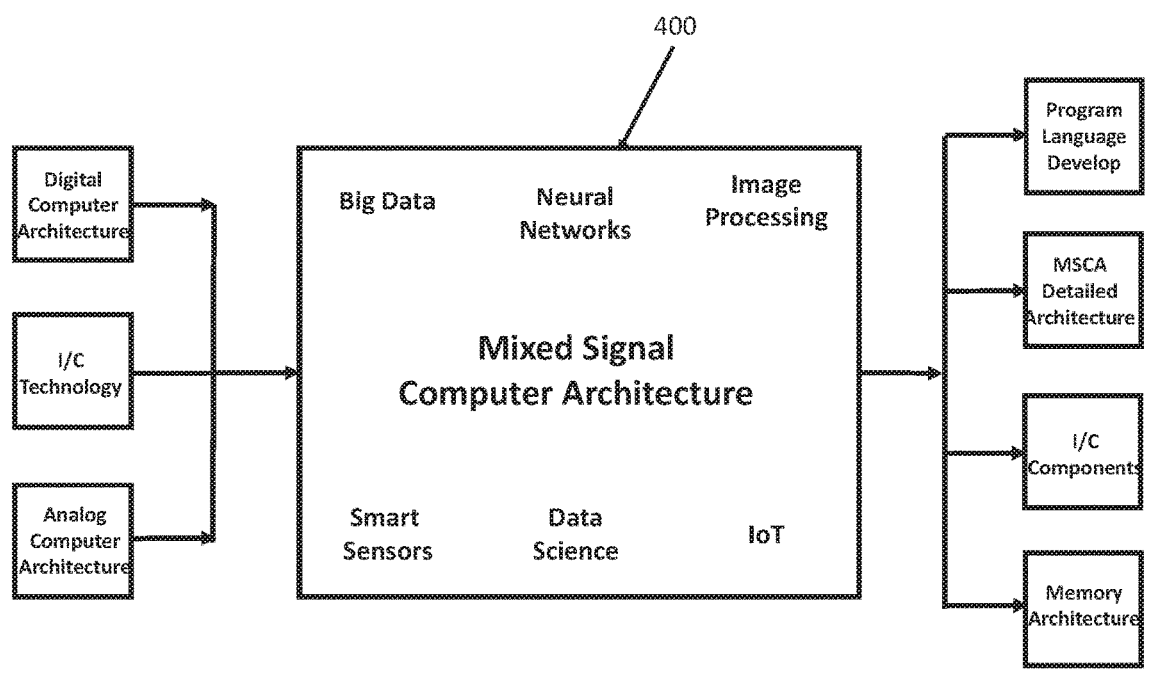
FIG. 13 depicts a mixed signal computer architecture according to some embodiments.

FIG. 13 illustrates an embodiment of the MSCA 400 implementing embodiments described herein. As shown in FIG. 13, the embodiments described herein may be applicable, for instance, to data processing directed to Big Data, Neural Network, Image processing, Smart Sensors, Data Science, and IoT.

Figure 14:
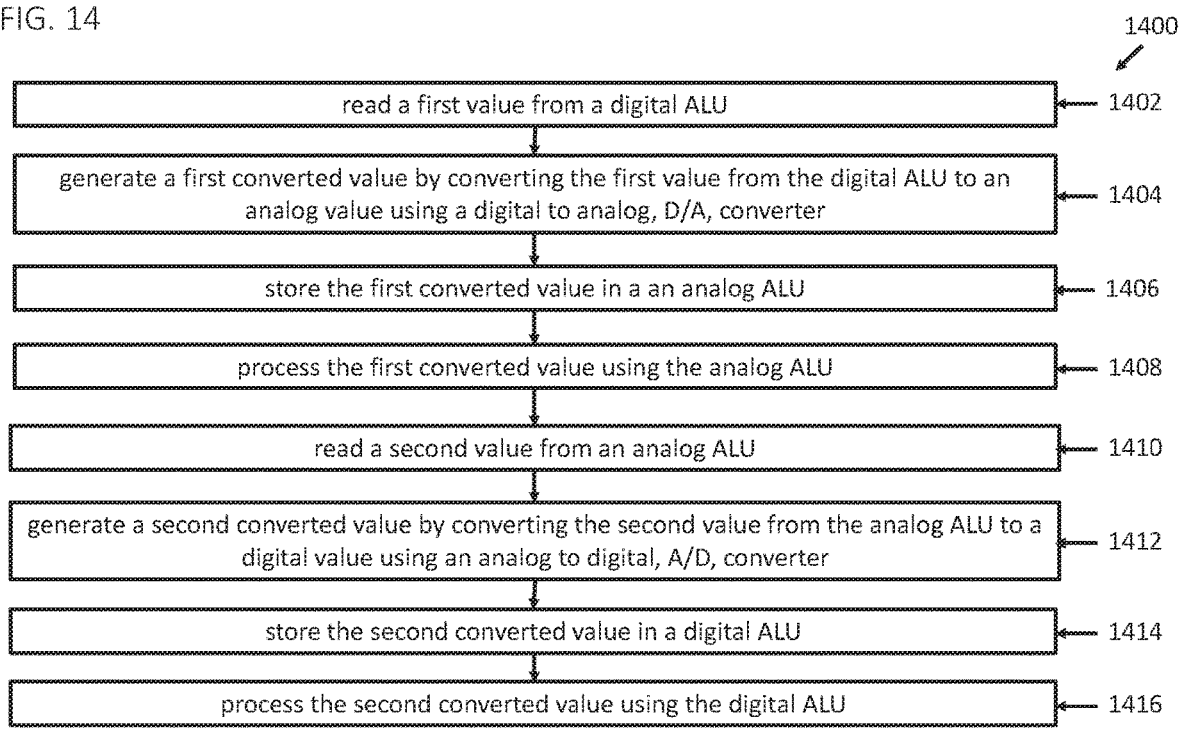
FIG. 14 is a flow chart depicting a process according to some embodiments.

FIG. 14 is a flow chart illustrating a process 1400, according to some embodiments, for performing mixed signal computations. The process 1400 may begin with step 1402 in which a first value is read from a digital ALU. In step 1404, a first converted value is generated by converting said first value from said digital ALU to an analog value using a digital to analog, D/A, converter. In step 1406, the first converted value is stored in an analog ALU. In step 1408, the first converted value is processed using the analog ALU. In step 1410, a second value is read from an analog ALU. In step 1412, a second converted value is generated by converting the second value from the analog ALU to a digital value using an analog to digital, A/D, converter. In step 1414, the second converted value is stored in a digital ALU. In step 1416, the second converted value is processed using the digital ALU.

In some embodiments, the digital ALU includes one or more registers and the analog ALU comprises one or more registers. In some embodiments, at least one of the converting and storing includes the use of an exchange register.

In some embodiments, the process 1400 includes a further step in which a magnitude of an analog value is adjusted with an automatic gain control circuit and a digital value is normalized with a shifter. In some embodiments, the values are adjusted to a maximum range of corresponding analog and digital memories.

Figure 15:
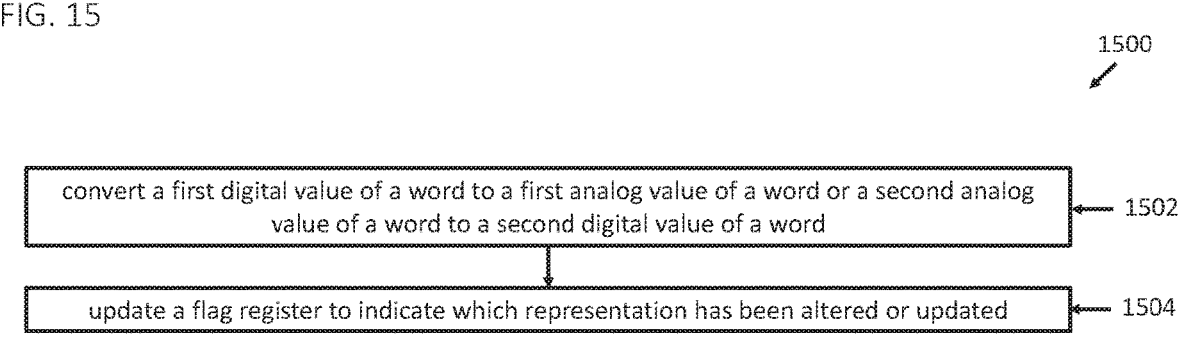
FIG. 15 is a flow chart depicting a process according to some embodiments.

FIG. 15 is a flow chart illustrating a process 1500, according to some embodiments, for synchronizing a digital data word and an analog data word. The process 1500 may begin with step 1502 in which a first digital value of a word is converted to a first analog value of a word or a second analog value of a word to a second digital value of a word. In step 1504, a flag register is updated to indicate which value has been converted. In some embodiments, the converting is performed based at least in part on a determination that an analog or digital representation is missing or that at least one of the first digital value or the second analog value is wrong or erased.

Figure 16:
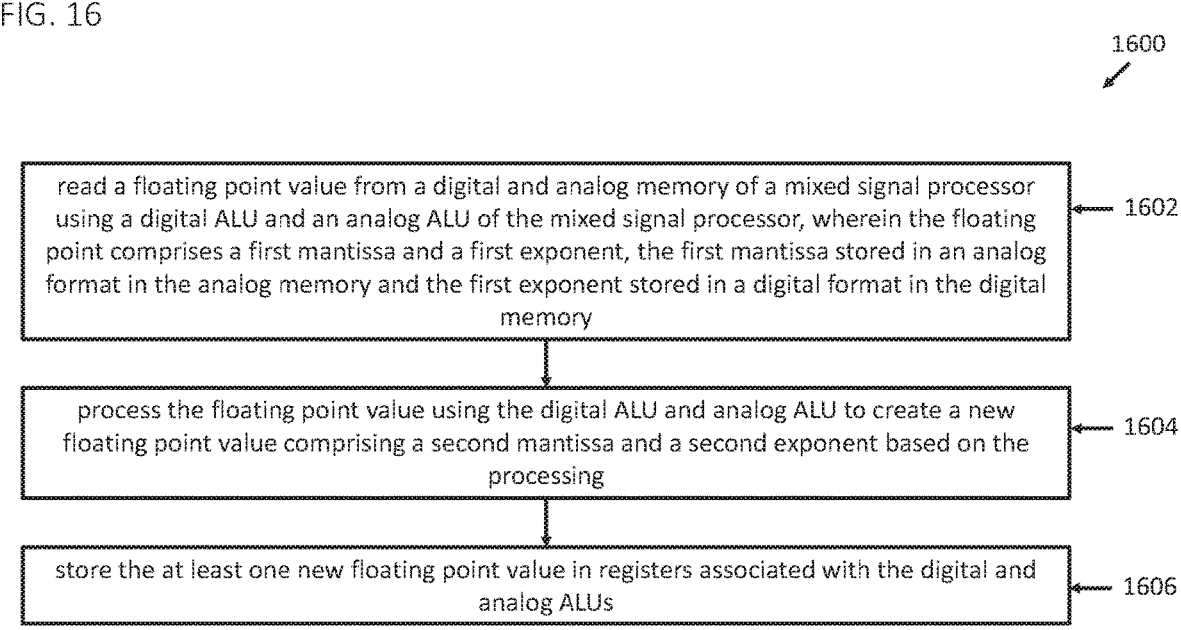
FIG. 16 is a flow chart depicting a process according to some embodiments.

FIG. 16 is a flow chart illustrating a process 1600, according to some embodiments, for performing floating point operations using a mixed signal computer. The process 1600 may begin in step 1602 in which a floating point value is read from a digital and analog memory of the mixed signal processor using a digital ALU and an analog ALU of the mixed signal processor, wherein the floating point comprises a first mantissa and a first exponent, the first mantissa stored in an analog format in the analog memory and the first exponent stored in a digital format in the digital memory. In step 1604, said floating point value is processed using the digital ALU and analog ALU to create a new floating point value comprising a second mantissa and a second exponent based on the processing. In step 1606, the new floating point value is stored in registers associated with the digital and analog ALUs, wherein the second mantissa is stored in the analog format in the analog memory and the second exponent is stored in the digital format in the digital memory.

The processes described above, for example in FIGS. 14-16, may be performed using one or more of the foregoing devices, systems, and or flows. According to some embodiments, the disclosed devices, systems, and processes may be implemented using a non-transitory computer readable medium storing computer code for processing a set analog and digital input signals, the computer code being executable by a processor, such as a mixed signal processor, to cause the processor to perform one or more of the foregoing. In some aspects, a memory and processor are provided, where the memory includes instructions executable by the processor to perform one or more of the foregoing.

Figure 17:
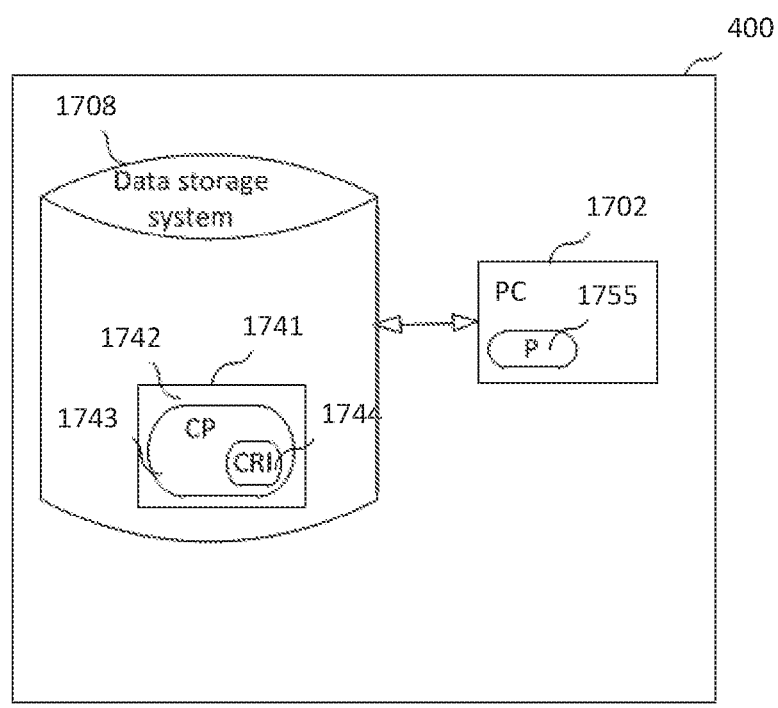
FIG. 17 is a block diagram of an embodiment for a Mixed Signal Computer Architecture.

FIG. 17 is a block diagram of MSCA 400 according to some embodiments. As shown in FIG. 17, MSCA 400 may comprise: a processing circuitry (PC) 1702, which may include one or more processors (P) 1755 (e.g., a general purpose microprocessor and/or one or more other processors, such as an application specific integrated circuit (ASIC), field-programmable gate arrays (FPGAs), and the like); and local storage unit (a.k.a., "data storage system") 1708, which may include one or more non-volatile storage devices and/or one or more volatile storage devices (e.g., random access memory (RAM)). In embodiments where MSCA 400 includes a general purpose microprocessor, a computer program product (CPP) 1741 may be provided. CPP 1741 includes a computer readable medium (CRM) 1742 storing a computer program (CP) 1743 comprising computer readable instructions (CRI) 1744. CRM 1742 may be a non-transitory computer readable medium, such as, but not limited to, magnetic media (e.g., a hard disk), optical media, memory devices (e.g., random access memory), and the like. In some embodiments, the CRI 1744 of computer program 1743 is configured such that when executed by processing circuitry 1702, the CRI causes MSCA 400 to perform steps described above (e.g., steps described above with reference to the flow charts). In other embodiments, MSCA 400 may be configured to perform steps described herein without the need for code. That is, for example, processing circuitry 1702 may include one or more ASICs. Hence, the features of the embodiments described herein may be implemented in hardware and/or software.

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A mixed signal computer, comprising:
one or more digital ALUs;
one or more digital registers, wherein at least one of said digital registers is connected to least one of said digital ALUs;
one or more analog ALUs;
one or more analog registers, wherein at least one of said analog registers is connected to least one of said analog ALUs;
one or more exchange registers, wherein said exchange registers are interconnected with at least one of said digital registers and at least one of said analog registers; and
a control unit, wherein said control unit is configured to control said one or more digital ALUs, said one or more analog ALUs, and said one or more exchange registers;
a digital memory; and
an analog memory,
wherein said control unit is configured such that analog data words are written into both said analog and said digital memories using the same address location, and
wherein data written into said analog memory is converted to a digital format and stored at the corresponding address location in said digital format in said digital memory.

2. The mixed signal computer of claim 1, further comprising:
a plurality of inputs, wherein at least one of said inputs is analog and at least one of said inputs is digital; and
a plurality of outputs, wherein at least one of said outputs is analog and at least one of said outputs is digital.

3. The mixed signal computer of claim 1, wherein said one or more analog ALUs operate continuously responsive to a set of instructions from the control unit using a clock signal independent of the clock signal operating said one or more digital ALUs.

4. The mixed signal computer of claim 1, further comprising:
an automatic gain control circuit controlled by said control unit to scale data values stored in said analog memory; and a data shifter controlled by said control unit to scale data values stored in said digital memory.

5. The mixed signal computer of claim 1, wherein:
a mantissa of a data value is stored in said analog memory, and
an exponent for said mantissa of a stored value is stored in said digital memory.

6. The mixed signal computer of claim 1, wherein a flag is set in a register indicating said conversion.

7. The mixed signal computer of claim 1, wherein said control unit is configured such that digital data words are written into both said analog and said digital memories using the same address location for the corresponding memory array, wherein data written into said digital memory is converted to an analog format and stored at the corresponding address location in said analog format in said analog memory.

8. The mixed signal computer of claim 7, wherein a flag is set in a register indicating said conversion.

9. The mixed signal computer of claim 1, wherein said analog and digital ALUs are selectively synchronized based on at least one of the following: a sample clock, an instruction from said control unit, or an interrupt.

10. The mixed signal computer of claim 1, wherein a set of registers are employed to identify when one or more of an analog memory location is refreshed based on its digital counterpart, a digital memory location is refreshed based on its analog counterpart, a digital memory location is refreshed based on an equivalent memory update, and an analog memory location is directly refreshed.

11. The mixed signal computer of claim 1, wherein said digital ALU is provided with intermediate results from said analog ALU, based on at least one of the following: a predetermined instruction from said control unit, a clock set up by said control unit, and a predetermined interrupt set up by said control unit.

12. The mixed signal computer of claim 1, wherein said analog ALU is provided with intermediate results from said digital ALU, responsive to a predetermined instruction from said control unit.

13. The mixed signal computer of claim 1, wherein each analog ALU comprises:
one or more analog registers, and
wherein each analog ALU is configured to perform at least one arithmetic operation and at least one logic operation.

14. The mixed signal computer of claim 13, wherein said logic operations comprise:
a greater than operation and a less than operation,
a load operation and a store operation, and
at least one of an Or, And, Exclusive Or, Nor, Nand, or Invert operation.

15. A mixed signal computer, comprising:
one or more digital ALUs;
one or more digital registers, wherein at least one of said digital registers is connected to least one of said digital ALUs;
one or more analog ALUs;
one or more analog registers, wherein at least one of said analog registers is connected to least one of said analog ALUs; and
one or more exchange registers, wherein said exchange registers are interconnected with at least one of said digital registers and at least one of said analog registers,
wherein a set of registers are employed to identify when one or more of an analog memory location is refreshed based on its digital counterpart, a digital memory location is refreshed based on its analog counterpart, a digital memory location is refreshed based on an equivalent memory update, and an analog memory location is directly refreshed.

16. A mixed signal computer, comprising:
one or more digital ALUs;
one or more digital registers, wherein at least one of said digital registers is connected to least one of said digital ALUs;
one or more analog ALUs;
one or more analog registers, wherein at least one of said analog registers is connected to least one of said analog ALUs;
one or more exchange registers, wherein said exchange registers are interconnected with at least one of said digital registers and at least one of said analog registers;
a control unit, wherein said control unit is configured to control said one or more digital ALUs, said one or more analog ALUs, and said one or more exchange registers;
a digital memory; and
an analog memory,
wherein said control unit is configured such that digital data words are written into both said analog and said digital memories using the same address location for the corresponding memory array, and
wherein data written into said digital memory is converted to an analog format and stored at the corresponding address location in said analog format in said analog memory.

17. The mixed signal computer of claim 16, wherein a flag is set in a register indicating said conversion.

* * * * *